United States Patent
Saleem

(10) Patent No.: US 9,726,657 B2
(45) Date of Patent: Aug. 8, 2017

(54) PULLOUT APPARATUS AND SYSTEM FOR TESTING OF ANCHOR BOLTS/BARS

(71) Applicant: UNIVERSITY OF DAMMAM, Dammam (SA)

(72) Inventor: Muhammad Saleem, Dammam (SA)

(73) Assignee: UNIVERSITY OF DAMMAM, Dammam (SA)

( * ) Notice: Subject to any disclaimer, the term of this patent is extended or adjusted under 35 U.S.C. 154(b) by 0 days.

(21) Appl. No.: 14/594,509

(22) Filed: Jan. 12, 2015

(65) Prior Publication Data
US 2016/0202232 A1    Jul. 14, 2016

(51) Int. Cl.
   G01N 3/08    (2006.01)
   G01N 33/38   (2006.01)

(52) U.S. Cl.
   CPC ............ G01N 33/383 (2013.01); G01N 3/08 (2013.01)

(58) Field of Classification Search
   CPC ............................... G01N 3/08; G01N 33/383
   USPC .......................................... 73/803, 856, 827
   See application file for complete search history.

(56) References Cited

U.S. PATENT DOCUMENTS

| | | | | |
|---|---|---|---|---|
| 5,438,863 A * | 8/1995 | Johnson | ................... | G01N 3/08 73/150 A |
| 5,948,994 A * | 9/1999 | Jen | ........................... | G01N 3/08 73/796 |
| 2002/0017146 A1* | 2/2002 | Oliver | ...................... | G01N 3/08 73/856 |
| 2010/0011873 A1* | 1/2010 | Kaneda | ................... | G01N 3/02 73/788 |

(Continued)

FOREIGN PATENT DOCUMENTS

| CN | 101852700 B | 11/2011 |
|---|---|---|
| CN | 102677710 A * | 9/2012 |

(Continued)

OTHER PUBLICATIONS

Machine translation of Bibliographic Data and Abstract in English of CN102677710, data: Sep. 19, 2012; Translation by ESPACENET, total pp. 8.*

(Continued)

*Primary Examiner* — Lisa Caputo
*Assistant Examiner* — Roger Hernandez-Prewitt
(74) *Attorney, Agent, or Firm* — Oblon, McClelland, Maier & Neustadt, L.L.P.

(57) ABSTRACT

A pullout test system, having a pullout apparatus including a plurality of bracing rods connected to a first support plate at proximal end of the plurality of bracing rods and a second base plate connected at a distal end of the plurality of bracing rods. The apparatus also includes a reaction rod attached to the first base plate extending away from the plurality of bracing rods. The apparatus further includes a sample specimen mounting location disposed centrally on the second base plate and disposed between the first base plate and the second base plate and an anchor disposed through the second base plate and fixed within the sample specimen disposed centrally on the second base plate. The system includes a universal testing machine (UTM). The pullout apparatus is configured to be mounted within the UTM via the anchor and the reaction rod to apply tensile forces thereto.

17 Claims, 8 Drawing Sheets

(56) References Cited

U.S. PATENT DOCUMENTS

2013/0055823 A1* 3/2013 Kawano ............... G01N 3/08
73/805

FOREIGN PATENT DOCUMENTS

CN          202433253 U    9/2012
JP          2009-167753 A  7/2009

OTHER PUBLICATIONS

Author: Patrik Groth, Title: Fibre Reinforced Concrete—Fracture Mechanics Methods Applied on Self-Compacting Concrete and Energetically Modified Binders, Date: Jan. 2000, Publisher: Lulea University of Technology, pp. 1-11, 40-51 and 106-147.*
Author: unknown, 1 web page showing Figure 2. Schematic diagram for Dartec machine, Publisher: ResearchGate, Date fig. published: 2003 in International Journal of Fracture, vol. 120, pp. 501-515 to Mourad, A-H. et al. under Ultra high molecular weight polyethylene deformation and fracture behaviour as a function of high strain rate.*
Author: Brian Knight, Title: Testing large bonded-in fasteners, Date: Yr. 2002, Publisher: Gougeon Brothers, Publication: Building, Restoration & Repair with Epdxy, Epoxyworks, No. 19, pp. 4.*

* cited by examiner

PULLOUT APPARATUS AND SYSTEM FOR TESTING OF ANCHOR BOLTS/BARS

BACKGROUND

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

In construction technology, pullout testing generally establishes the holding force of anchors and fixings in most construction materials, such as concrete. In conventional pullout testing of anchor bolts/bars require applying a specific tensile load to an anchor bolt/bar in order that the bolt/bar can sustain such a test condition for a period of time. Deformation of the anchor tested can also be measured to understand the relationship between force and displacement during testing.

Further, the time, effort, cost, and equipment needed to conduct conventional pullout testing can be extensive and tedious, requiring skilled labor, a linear variable displacement transducer (LVDT), a data acquisition system, and hydraulic pumps with pressure gauges. Conventional material testing and quality assurance may play a pivotal role in every major construction project. Currently, for large scale projects an on-site material testing and quality assurance lab may be established. Hence, quick, reliable and effective methods and apparatuses are preferred to achieve the quantitative analysis of material strength fixed to ground.

For example, FIG. 1 is a schematic view of a conventional pullout apparatus 100 for pullout testing of anchor bolts/bars from a concrete structure 130. In FIG. 1, the conventional pullout apparatus 100 is attached via a weld point 120 to an anchor 125 embedded in concrete 130 or the like. Hydraulic feed lines 110 are connected to a center hold jack 115 or the like. A load cell 105 is disposed atop the center hold jack 115 with a support rod 107 which is connected to the weld point 120 and passes through load cell 105 and jack 115. Load cell 105 is connected to an output line 113 which is configured to read the load applied to anchor 125 during testing. The anchor 125 may be disposed in a concrete block or wall 130 for pullout testing purposes. The load cell 105 may be a LVDT and the output line 113 may be connected to a data acquisition system (not shown). Further, feed lines 110 may be connected to pressure gauges (not shown).

SUMMARY

Embodiments include a pullout apparatus, having a plurality of bracing rods connected to a first base plate at a proximal end of the plurality of bracing rods. The apparatus also includes a second base plate connected at a distal end of the plurality of bracing rods. The apparatus further includes a reaction rod attached to the first base plate extending away from the plurality of bracing rods. The apparatus also includes a sample specimen mounting location disposed between the first base plate and the second base plate. The apparatus further includes an anchor disposed through the second base plate and configured to be fixed within a sample specimen mounted at the sample specimen mounting location.

Embodiments include a pullout test system, having a pullout apparatus. The pullout apparatus includes a plurality of bracing rods connected to a first base plate at proximal end of the plurality of bracing rods. The apparatus also includes a second base plate connected at a distal end of the plurality of bracing rods. The apparatus further includes a reaction rod attached to the first base plate extending away from the plurality of bracing rods. The apparatus also includes a sample specimen mounting location disposed between the first base plate and the second base plate. The apparatus further includes an anchor disposed through the second base plate and configured to be fixed within a sample specimen mounted at the sample specimen location. The pullout test system includes a universal testing machine (UTM) connected to the pullout apparatus.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
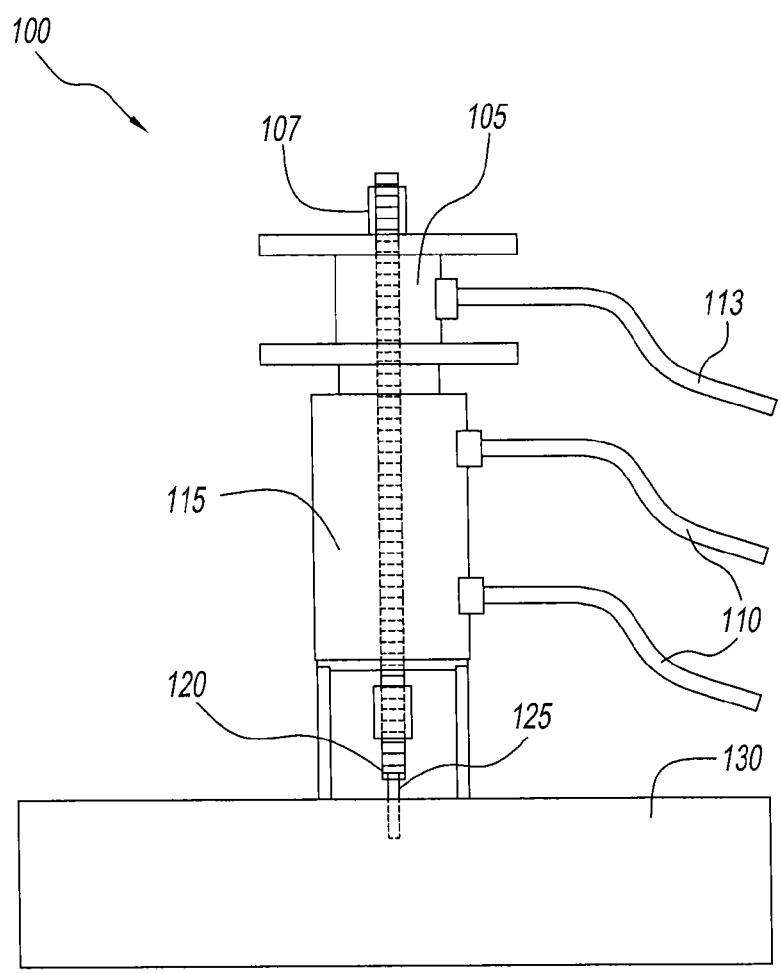
FIG. 1 is a schematic view of a conventional pullout apparatus for pullout testing of anchor bolts/bars from a concrete structure.

Referring now to the drawings, wherein like reference numerals designate identical or corresponding parts throughout the several views.

Pullout apparatuses 200 or 201 as shown in FIGS. 2A to 2D and a universal testing machine (UTM) 300 as shown in FIG. 3 can be configured, for example, to conduct anchor pullout strength testing of specimens. Traditionally, such testing requires a hydraulic jack, pressure gauge, data acquisition system (DAS), data storage and management system (DSMS), LVDT and specialized manpower as shown in FIG. 1. However, using the pullout apparatuses 200 or 201 coupled with the UTM 300, the above mentioned traditional equipment can be replaced and the laboratory pullout strength testing for concrete anchor bars and anchor bolts can be made time and cost effective, efficient and will not require specialized labor. Furthermore, by utilizing the data acquisition, management and storage system embedded in the UTM 300, the need of separate data storage and management device can be eradicated and real-time displacement verses strength graph can be obtained.

Pullout apparatuses 200 or 201 can be used to carry out pullout testing of an anchor rod/bar 225 using the universal testing machine 300 whereas traditional testing practice is to use an assembly of hydraulic jack, reaction frame, load cells and data acquisition system, which is expensive to setup and requires skilled labor. On the other hand, using the pullout apparatus 200 of the present disclosure will result in a simple setup without the need for a complex reaction frame, load cell, hydraulic jack and data acquisition system, which will lead to a much more economical pullout test. Further, the pullout apparatus 200 results in a non-destructive test to evaluate the load carrying capacity of the anchor rod/bar 225.

Figure 2A:
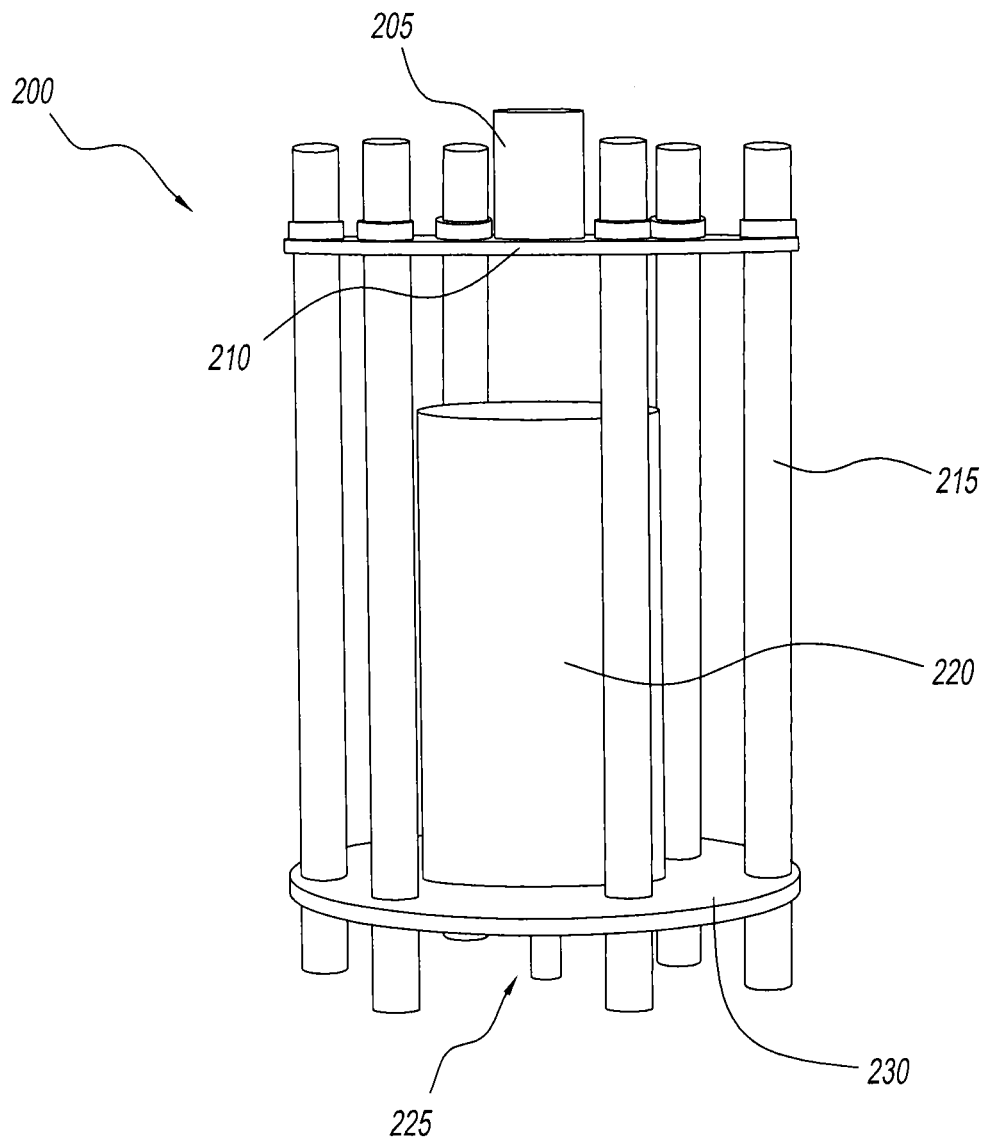
FIG. 2A is a perspective view of a pullout apparatus for pullout testing of anchor bolts/bars from a specimen according to certain embodiments of the disclosure.

FIG. 2A is a perspective schematic view of a pullout apparatus 200 for pullout testing of anchor bolts/bars from a specimen according to certain embodiments of the disclosure. In FIG. 2A, pullout apparatus 200 includes a reaction rod 205, a first metal support plate 210, a plurality of bracing rods 215, a specimen 220, an anchor 225, and a second metal support plate 230.

In some embodiments the first metal support plate 210 and the second metal support plate 230 are comprised of high strength steel or the like to withstand the tensile forces applied to the anchor 225. Anchor 225 may be configured as a bolt, rod or bar and embedded within specimen 220. Specimen 220 may comprise various forms of reinforced concrete, such as that found in various support structures, for example, garage floors, and other building structures. Also, specimen 220 may be configured as a cylinder to be mounted within pullout apparatuses 200 or 201 at the second metal support plate 230, as shown in FIGS. 2A and 2C.

Reaction rod 205 may comprise a high strength steel rod or bar welded to the first metal support plate 210. The plurality of bracing rods 215 may include a number of spaced-apart metal rods comprised of high strength steel welded at their distal ends to the second metal support plate 230 and having screw threaded proximal ends with bolted on nuts above and below the plane of the first metal support plate 210. Thus, the first metal support plate 210 is configured to be removable from pullout apparatus 200. Alternatively, second metal support plate 230 may be similarly configured to be removable from pullout apparatus 200. Further, first and second metal support plates 210, 230 are arranged in parallel planes to each other in exemplary embodiments. Also, in some embodiments, first and second metal support plates 210, 230 may be configured to be fixed to the plurality of bracing rods 215 via welds or via bolted on nuts.

Figure 2B:
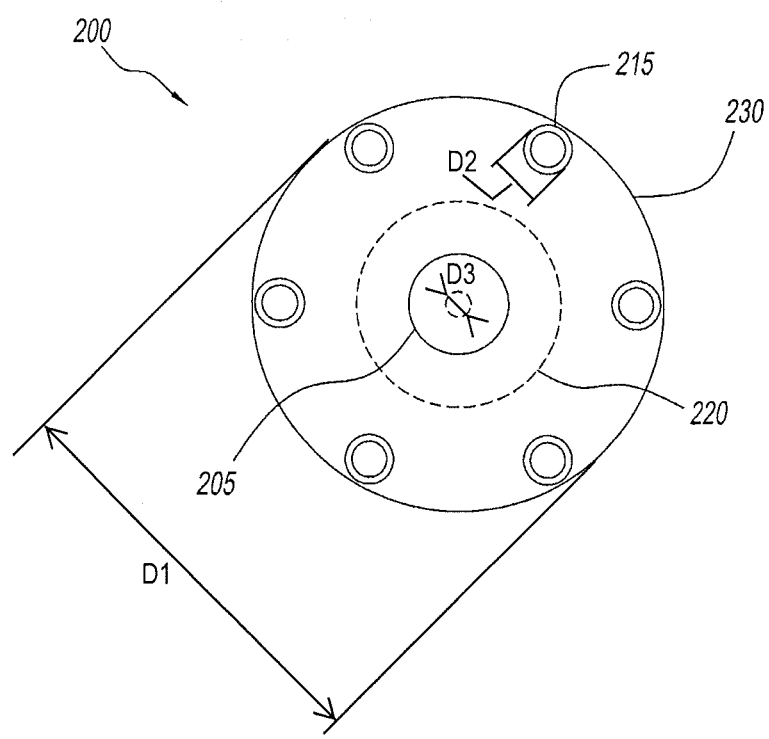
FIG. 2B is a top schematic view of the pullout apparatus of FIG. 2A according to certain embodiments of the disclosure.
Figure 2C:
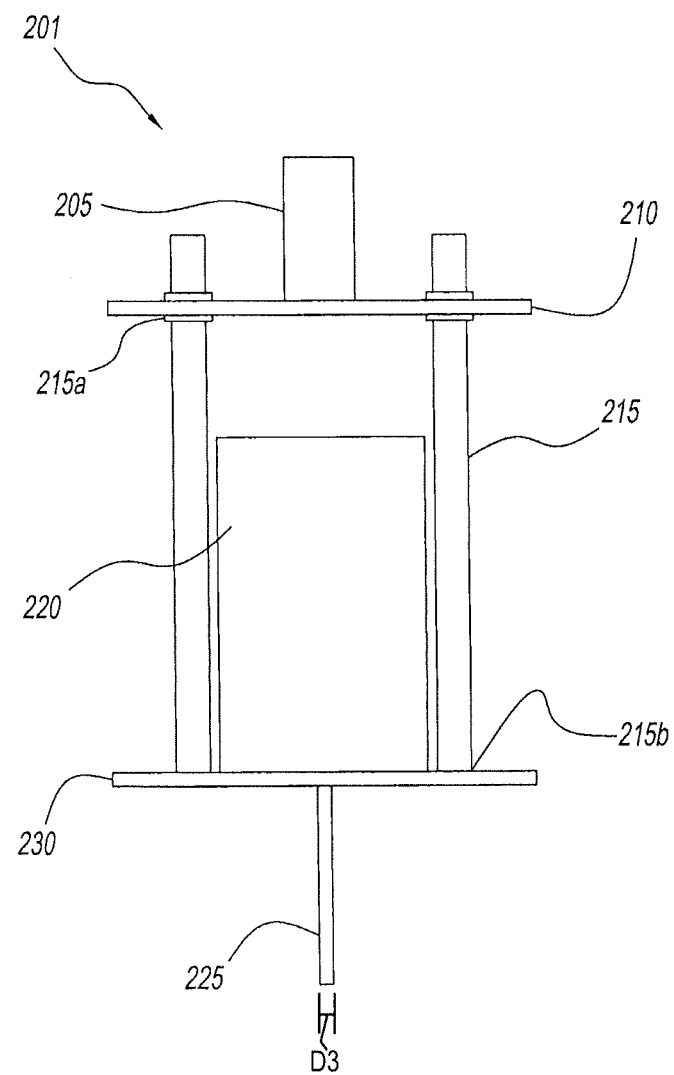
FIG. 2C is a schematic side view of a pullout apparatus according to another embodiment of the disclosure.

FIG. 2B is a top schematic view of the pullout apparatus 200 of FIG. 2A according to certain embodiments of the disclosure. In FIG. 2B, the plurality of bracing rods 215 are shown in relation to the reaction rod 205, the second metal support plate 230 and the concrete cylinder specimen 220. It should be noted that the second metal support plate 230, the concrete cylinder specimen 220 and the reaction rod 205 are coaxially arranged in the pullout apparatus 200 to more evenly distribute tensile forces during testing. Further, in FIG. 2B, the plurality of bracing rods 215 are shown to be six rods, however, a configuration of at least two rods may suffice based on the amount of tensile forces to be applied to the specimen during testing.

In some embodiments, the bracing rods 215 may diametrically measure (D2) at or about 25 millimeters (mm), the anchor 225 may diametrically measure (D3) at or about 20 with a maximum of 25 mm, the first and second steel support plates 210, 230 may diametrically measure (D1) at or about 300 mm, and the specimen 220 may diametrically measure at or about 150 mm, for example. These dimensions may provide maximum rigidity of pullout apparatus 200 while minimizing the amount and cost of materials used during testing. Of course, other proportionally related dimensions may be used depending on the tests to be run and the materials comprising the specimen 220 and the anchor 225. Furthermore, second metal support plate 230 includes an opening having a diameter at or about 30 mm, the opening being configured to allow the embedded anchor 225 to pass there through.

FIG. 2C is a schematic view of a pullout apparatus 201 according to another embodiment of the disclosure. In FIG. 2C, pullout apparatus 201 includes a pair of mounting nuts 215a screwed onto the proximal ends of each of the plurality of bracing rods 215 at locations immediately above and below the first metal support plate 210. Further, the plurality of bracing rods 215 are welded at 215b to the second metal support plate 230. Weld 215b coincides with the distal ends of the plurality of bracing rods 215. In this configuration, the first metal support plate 210 may be removable and/or replaceable in order to accommodate different configurations or changes in the sample specimen's size or material as well as accommodating any different spaced bracing rod configurations.

Figure 2D:
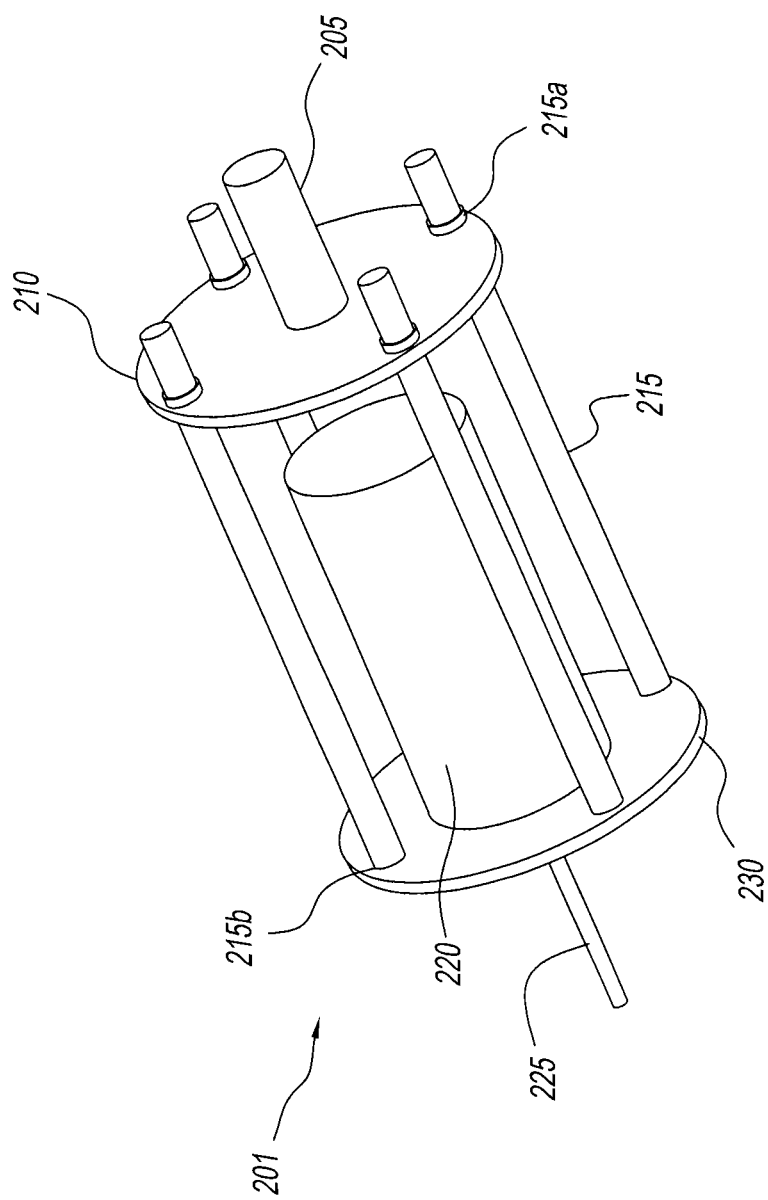
FIG. 2D is a perspective view of the pullout apparatus of FIG. 2C according to another embodiment of the disclosure.

FIG. 2D is a perspective view of the pullout apparatus 201 of FIG. 2C according to another embodiment of the disclosure. In FIG. 2D, the pullout apparatus 201 may be configured such that, for example, the reaction rod 205 diametrically measures at or about 25 mm, the bracing rods 215 diametrically measure at or about 25 mm, the first and second metal support plates 210, 230 diametrically measure at or about 300 mm with a thickness in the axial direction of the bracing rods 215 of at or about 25 mm, and the specimen 220 diametrically measures at or about 150 mm across and measures at or about 300 mm in an axial direction. These dimensions may provide maximum rigidity of pullout apparatus 201 while minimizing the amount and cost of materials used during testing. In some embodiments, the thicknesses of the first and second metal support plates 210, 230 may be configured such that the first metal support plate 210 is thicker in an axial direction than the second metal support plate 230 to provide increased strength when apparatus 201 is placed under tension during a pullout test.

Figure 3A:
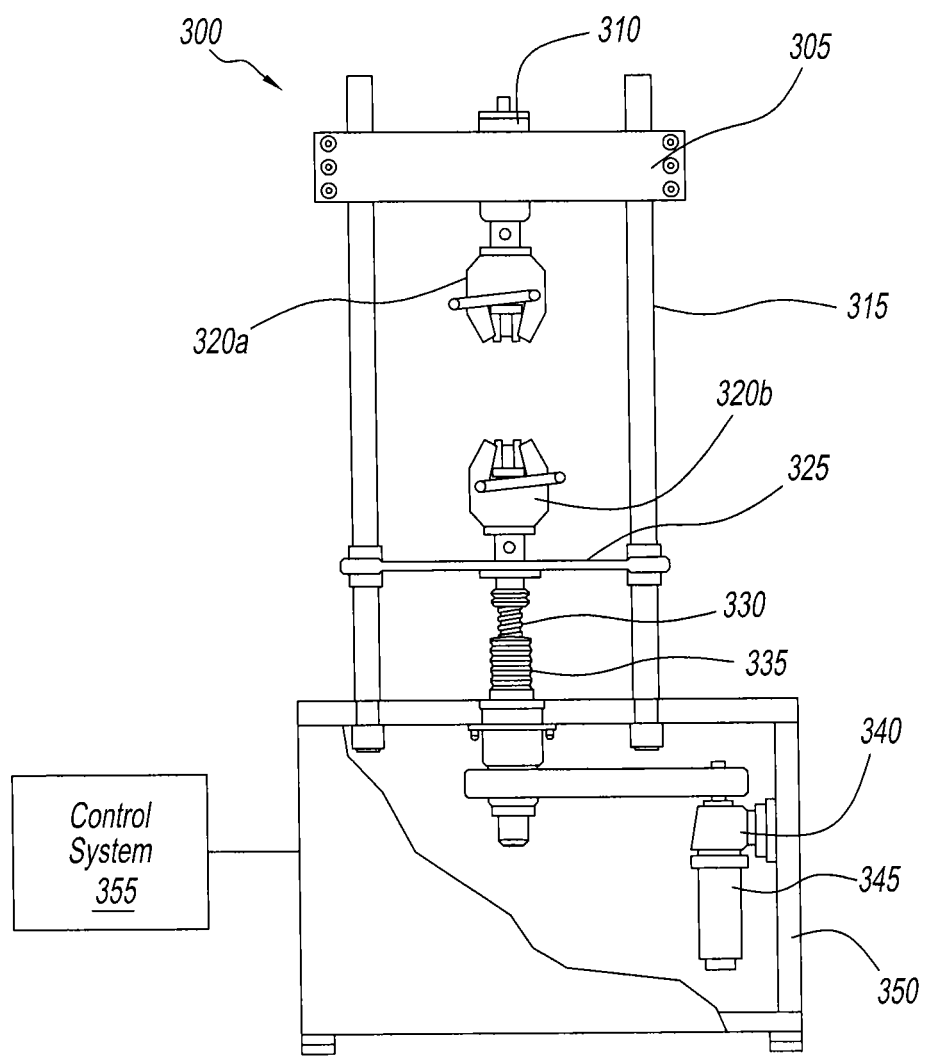
FIG. 3A is a schematic view of a universal testing machine (UTM) according to certain embodiments of the disclosure.

FIG. 3A is a schematic view of a universal testing machine (UTM) 300 according to certain embodiments of the disclosure. In FIG. 3, the UTM 300 includes a first crosshead 305, a load cell 310, support columns 315, a first grip 320a, a second grip 320b, a second crosshead 325, a recirculating ball screw system 330, a protective sleeve 335, a gearbox 340, a DC/AC servomotor 345, a base support 350, and a control system 355.

In certain embodiments, the first and second crossheads 305, 325 may be configured as movable members controlled to move up or down, usually at a constant speed. Some universal testing machines may program the crosshead speed or conduct cyclical testing, testing at constant force, testing at constant deformation, etc. Further, electromechanical, servo-hydraulic, linear drives, and resonance drives may be used. Load cell 310 is a force transducer or the like configured to measure an applied load. Load cell 310 may require period calibration to maintain its accuracy.

Support columns 315, often referred to as the load frame, may consist of two strong supports for the UTM 300. First grip 320a and second grip 320b may be configured as tensile test grips or specimen holding jaws for performing a tensile test or the like.

Figure 3B:
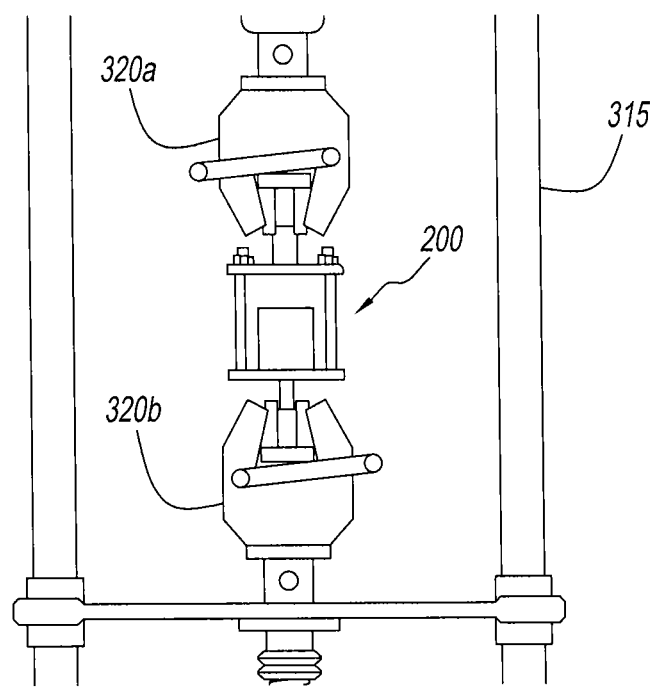
FIG. 3B is a partial schematic view of the universal testing machine (UTM) of FIG. 3A showing the pullout apparatuses of FIGS. 2A to 2D mounted therein according to certain embodiments of the disclosure.

FIG. 3B is a partial schematic view of the universal testing machine (UTM) 300 of FIG. 3A showing the pullout apparatus 200 of FIGS. 2A to 2D mounted therein according to certain embodiments of the disclosure. In FIG. 3B, the pullout apparatus 200 is securely mounted between grips 320a and 320b to perform a tensile test via the UTM 300. In this embodiment, reaction rod 205 is mounted in grip 320a and anchor 225 is mounted in grip 320b. When an operator activates the control system 355 for tensile testing, grip 320a may remain fixed while grip 320b may be configured to move away from grip 320a via the movement of the second crosshead 325 in an opposing direction to first crosshead 305. As the grips 320a and 320b move farther apart load cell 310 is configured to measure the applied load via force transducers (not shown) while the control system 355 records the load data and the displacement data during each test until anchor 225 is pulled out of specimen 220 or any other test constraints or conditions are met. Alternatively, grip 320a may be configured to move while grip 320b remains fixed or both grips 320a, 320b may be configured to move in opposing directions. DC/AC servomotor 345 is configured to cause gearbox 340 to rotate a drive belt which in turn causes the recirculating ball screw system 330 to move crosshead 325 up or down along support columns 315 during operation, thereby moving grip 320b.

Figure 4:
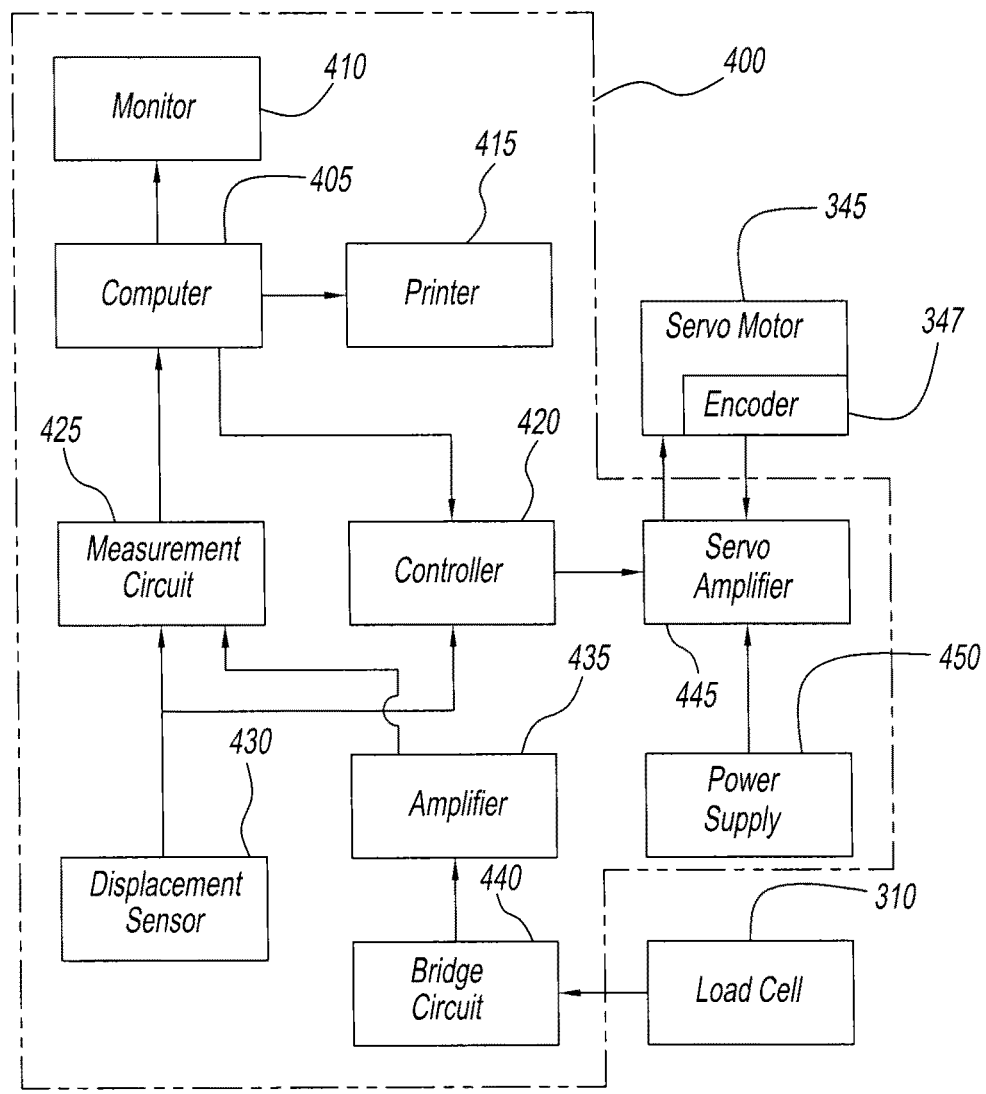
FIG. 4 is a block diagram of a control system for the UTM according to certain embodiments of the disclosure.

FIG. 4 is a block diagram of a control system 400 for the universal testing machine (UTM) 300 according to certain embodiments of the disclosure. In FIG. 4, the control system 400 (similar to control system 355 of FIG. 3A) includes a computer 405, a monitor 410, a printer 415, a controller 420, a measuring circuit 425, a displacement sensor 430, an amplifier 435, a bridge circuit 440, a servo amplifier 445, and a power supply 450. In some embodiments, the load cell 310 and the DC servomotor 345 having an encoder 347 are connected to the control system 400.

In some embodiments, the control system 400 of the UTM 300 performs the driving control and the measurement process of the UTM 300. The servo amplifier 445 generates a driving current for driving the DC servomotor 345 from power supplied from the power supply 450 based on a target speed signal sent from the controller 420, and supplies the driving current to the servomotor 345. An encoder 347 for measuring the rotation speed of the servomotor 345 is provided on a drive shaft of the servomotor 345. The servo amplifier 445 executes the feedback control in which the power (e.g., a pulse width of the driving current in the case of the pulse width modulation) to be supplied to the servomotor 345 is adjusted based on the rotation speed of the drive shaft of the servomotor 345. With this configuration, the servomotor 345 is controlled so that the rotation speed of the drive shaft of the servomotor 345 becomes equal to the target speed.

An output of the load cell 310, which measures the load applied to the test piece, for example, the anchor bolt/bar 125, is input to the measurement circuit 425 via the bridge circuit 440 and the amplifier 435. Similarly, an output of the displacement sensor 430 for measuring the displacement of the test piece is input to the measurement circuit 425. The measurement circuit 425 executes an A-D conversion for the analog signals from the load cell 310 and the displacement sensor 430, and transmits the converted signals to the computer 405. The displacement sensor 430 may include a linear variable displacement transducer (LVDT) or the like.

The computer 405 is configured to plot a graph based on the load and displacement transmitted from the measurement circuit 425, and displays it on the monitor 410. For example, the computer 405 calculates the stress applied to the test piece from the measurement value of the load and the sectional area of the test piece which has been measured in advance, and calculates the distortion of the test piece from the measurement value of the displacement and the size (actually, the distance between the chucks) of the test piece in the applying direction of the load. Then, the computer 405 displays the plot of the stress-distortion curve in real-time. The computer 405 is also able to print out the plotted graph via printer 415.

By operating the computer 405, an operator of the universal testing machine 300 transmits an indication value of the moving speed of the second crosshead 325 to the controller 420. Based on the indication value of the moving speed and the displacement sent from the displacement sensor 430, the controller 420 calculates the target speed signal to be sent to the servo amplifier 445, and transmits the target speed signal to the servo amplifier 445. The displacement is measured from a predetermined datum which is recorded and stored by the computer 405.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, define, in part, the scope of the foregoing claim terminology such that no inventive subject matter is dedicated to the public.

The invention claimed is:

1. A pullout apparatus, comprising:
a plurality of bracing rods connected to a cylindrical first base plate at a proximal end of the plurality of bracing rods;
a cylindrical second base plate connected at a distal end of the plurality of bracing rods;
a reaction rod attached to the first base plate extending away from the plurality of bracing rods;
a sample specimen mounting location disposed between the first base plate and the second base plate; and
an anchor disposed through the second base plate and configured to be fixed within a sample cylindrical specimen mounted at the sample specimen mounting location, wherein the first base plate is removably attached to the plurality of bracing rods to insert additional bracing rods based on the mounted sample specimen, wherein the first cylindrical base plate has a diameter equal to a diameter of the second cylindrical base plate, the cylindrical specimen has a diameter equal to half the diameter of either one of the first base plate and the second base plate, and a diameter of each bracing rod is equal to a diameter of the anchor, and wherein the reaction rod and the anchor are configured to be mounted in a universal testing machine (UTM), the reaction rod being connected to a first grip of the UTM, and the anchor being connected to a second grip of the UTM.

2. The pullout apparatus according to claim 1, wherein the sample specimen mounting location is fixed on the second base plate.

3. The pullout apparatus according to claim 1, wherein the sample specimen is a concrete cylinder.

4. The pullout apparatus according to claim 3, wherein the reaction rod is attached at the first base plate coaxial to a central axis of the sample specimen mounting location.

5. The pullout apparatus according to claim 1, wherein the first base plate is thicker in an axial direction than the second base plate.

6. The pullout apparatus according to claim 1, wherein the diameter of the first cylindrical base plate is 300 mm, the diameter of the specimen is 150 mm, and the diameter of each of the bracing rod, and the anchor is 25 mm.

7. A pullout test system, comprising:
a pullout apparatus including
a plurality of bracing rods connected to a first cylindrical base plate at proximal end of the plurality of bracing rods,
a cylindrical second base plate connected at a distal end of the plurality of bracing rods,
a reaction rod attached to the first base plate extending away from the plurality of bracing rods,
a sample specimen mounting location disposed between the first base plate and the second base plate, and
an anchor disposed through the second base plate and configured to be fixed within a cylindrical sample specimen mounted at the sample specimen location, wherein the first base plate is removably attached to the plurality of bracing rods to insert additional bracing rods based on the mounted sample specimen, wherein the first cylindrical base plate has a diameter equal to a diameter of the second cylindrical base plate, the cylindrical specimen has a diameter equal to half the diameter of either one of the first base plate and the second base plate, and a diameter of each bracing rod is equal to a diameter of the anchor; and
a universal testing machine (UTM) connected to the pullout apparatus, wherein the reaction rod and the anchor are configured to be mounted in a universal testing machine (UTM), the reaction rod being connected to a first grip of the UTM, and the anchor being connected to a second grip of the UTM.

8. The pullout test system according to claim 7, wherein the sample specimen is a concrete cylinder.

9. The pullout test system according to claim 8, wherein the reaction rod is attached at the first base plate coaxial to a central axis of the concrete cylinder, and the anchor is coaxial to the central axis of the concrete cylinder.

10. The pullout test system according to claim 7, wherein the sample specimen mounting location is fixed on the second base plate.

11. The pullout test system according to claim 7, wherein the reaction rod is attached at the first base plate coaxial to a central axis of the sample specimen mounting location.

12. The pullout test system according to claim 7, wherein the first base plate is thicker in an axial direction than the second base plate.

13. The pullout test system according to claim 7, wherein the UTM further includes:
a pair of support columns,
a first movable crosshead mounted between the pair of support columns,
a second movable crosshead mounted between the pair of support columns, and
a load cell mounted on the first movable crosshead.

14. The pullout test system according to claim 7, wherein the UTM further includes:
a motor configured to cause the first and second grips to apply a tensile force to the mounted pullout apparatus at the anchor and the reaction rod, respectively.

15. The pullout test system according to claim 14, further comprising a load cell configured to apply the tensile force to the mounted pullout apparatus until the sample specimen dislocates from the anchor.

16. The pullout test system according to claim 7, wherein the UTM further includes:
a control system having an input/output device, wherein a tensile force and a displacement measured from a predetermined datum via a transducer are recorded and stored by the control system.

17. The pullout test system according to claim 7, wherein the plurality of bracing rods includes at least four bracing rods.

* * * * *